(12) United States Patent
Dace et al.

(10) Patent No.: US 11,707,326 B2
(45) Date of Patent: *Jul. 25, 2023

(54) SPINAL IMPLANT SYSTEM AND METHODS OF USE

(71) Applicant: WARSAW ORTHOPEDIC INC., Warsaw, IN (US)

(72) Inventors: Mark C. Dace, Collierville, TN (US); Richard Quinn Brown, Collierville, TN (US); Rodney Ray Ballard, Lakeland, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 519 days.

This patent is subject to a terminal disclaimer.

(21) Appl. No.: 16/916,768

(22) Filed: Jun. 30, 2020

(65) Prior Publication Data

US 2020/0330160 A1 Oct. 22, 2020

Related U.S. Application Data

(63) Continuation of application No. 15/896,957, filed on Feb. 14, 2018, now Pat. No. 10,751,127.

(51) Int. Cl.
*A61B 17/88* (2006.01)
*A61B 34/10* (2016.01)
(Continued)

(52) U.S. Cl.
CPC .......... *A61B 34/10* (2016.02); *A61B 17/7032* (2013.01); *A61B 34/37* (2016.02);
(Continued)

(58) Field of Classification Search
CPC ......... A61B 34/10; A61B 34/37; A61B 34/20; A61B 34/25; A61B 17/7032; A61B 17/00234; A61B 17/702; A61B 17/844; A61B 17/864; A61B 17/8645; A61B 2034/2055; A61B 2034/2063; A61B 2090/374; A61B 2090/376; A61B 2090/3762; A61B 2090/3764; A61B 2090/3966; A61B 2017/00004; A61B 2017/00261; A61B 2017/00398; A61B 2017/00867; A61B 2017/0088;
(Continued)

(56) References Cited

U.S. PATENT DOCUMENTS 10,751,127 B2* 8/2020 Dace .................. A61B 17/7035
2015/0157416 A1* 6/2015 Andersson ............. A61B 34/10
606/102

(Continued)

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A method comprises the steps of: imaging a patient anatomy; selecting an implant strategy for at least one bone fastener having a first member; registering the imaging of the patient anatomy with imaging of at least a portion of a robot; engaging the first member with tissue of the patient anatomy via robotic guidance according to the implant strategy; and subsequently, manipulating the patient anatomy. Systems, spinal constructs, implants and surgical instruments are disclosed.

20 Claims, 11 Drawing Sheets

(51) Int. Cl.
  *A61B 17/70* (2006.01)
  *A61B 34/37* (2016.01)
  *A61B 17/84* (2006.01)
  *A61B 90/00* (2016.01)
  *A61B 17/56* (2006.01)
  *A61B 17/00* (2006.01)
  *A61B 34/00* (2016.01)
  *A61B 34/20* (2016.01)
  *A61B 17/86* (2006.01)

(52) U.S. Cl.
  CPC ....... *A61B 17/00234* (2013.01); *A61B 17/702* (2013.01); *A61B 17/844* (2013.01); *A61B 17/864* (2013.01); *A61B 17/8645* (2013.01); *A61B 34/20* (2016.02); *A61B 34/25* (2016.02); *A61B 2017/00004* (2013.01); *A61B 2017/0073* (2013.01); *A61B 2017/0088* (2013.01); *A61B 2017/00261* (2013.01); *A61B 2017/00398* (2013.01); *A61B 2017/00867* (2013.01); *A61B 2017/00893* (2013.01); *A61B 2017/00933* (2013.01); *A61B 2017/564* (2013.01); *A61B 2034/2051* (2016.02); *A61B 2034/2055* (2016.02); *A61B 2034/2063* (2016.02); *A61B 2090/363* (2016.02); *A61B 2090/374* (2016.02); *A61B 2090/376* (2016.02); *A61B 2090/3762* (2016.02); *A61B 2090/3764* (2016.02); *A61B 2090/3966* (2016.02)

(58) Field of Classification Search
  CPC ........... A61B 2017/00893; A61B 2017/00933; A61B 2017/564
  USPC ................ 606/264–270, 279, 305, 308.86 A
  See application file for complete search history.

(56) References Cited

U.S. PATENT DOCUMENTS

| | | | |
|---|---|---|---|
| 2016/0235492 A1* | 8/2016 | Morard | A61B 17/1757 |
| 2017/0151022 A1* | 6/2017 | Jascob | A61B 5/062 |
| 2017/0252114 A1* | 9/2017 | Crawford | A61B 17/7089 |
| 2017/0348061 A1* | 12/2017 | Joshi | A61B 10/0275 |
| 2018/0147018 A1* | 5/2018 | Crawford | A61F 2/4455 |
| 2018/0200002 A1* | 7/2018 | Kostrzewski | G02C 7/049 |
| 2019/0350657 A1* | 11/2019 | Tolkowsky | A61B 34/20 |

* cited by examiner

SPINAL IMPLANT SYSTEM AND METHODS OF USE

CROSS-REFERENCE TO RELATED APPLICATIONS

This application is a continuation of U.S. patent application Ser. No. 15/896,957, filed Feb. 14, 2018, which is incorporated herein by reference, in its entirety.

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical instruments are employed, for example, to engage the fasteners for attachment to the exterior of two or more vertebral members. This disclosure describes an improvement over these prior technologies.

SUMMARY

In one embodiment, a method for treating a spine is provided. The method comprises the steps of: imaging a patient anatomy; selecting an implant strategy for at least one bone fastener having a first member; registering the imaging of the patient anatomy with imaging of at least a portion of a robot; engaging the first member with tissue of the patient anatomy via robotic guidance according to the implant strategy; and subsequently, manipulating the patient anatomy. In some embodiments, systems, spinal constructs, implants and surgical instruments are disclosed.

In one embodiment, the method comprises the steps of: pre-operatively generating a CT scan of a patient anatomy including at least one vertebra; selecting an implant strategy according to the CT scan for at least one bone screw shaft; generating fluoroscopic images of at least a portion of a robot; registering the CT scan with the fluoroscopic images; engaging the bone screw shaft with the vertebra via robotic guidance according to the implant strategy; subsequently, manipulating the patient anatomy; and manually engaging an implant receiver with the bone screw shaft to comprise a bone screw.

In one embodiment, the method comprises the steps of: imaging vertebral tissue; selecting an implant strategy for at least one bone screw shaft; registering the imaging of the vertebral tissue with imaging of a robot connected with the vertebral tissue; connecting a surgical driver with the bone screw shaft, the surgical driver including an image guide oriented relative to a sensor to communicate a signal representative of a position of the bone screw shaft; engaging the bone screw shaft with the vertebral tissue via robotic guidance according to the implant strategy; subsequently, manipulating the vertebral tissue; and manually engaging an implant receiver with the bone screw shaft to comprise a bone screw.

BRIEF DESCRIPTION OF THE DRAWINGS

The present disclosure will become more readily apparent from the specific description accompanied by the following drawings, in which.

DETAILED DESCRIPTION

Figure 1:
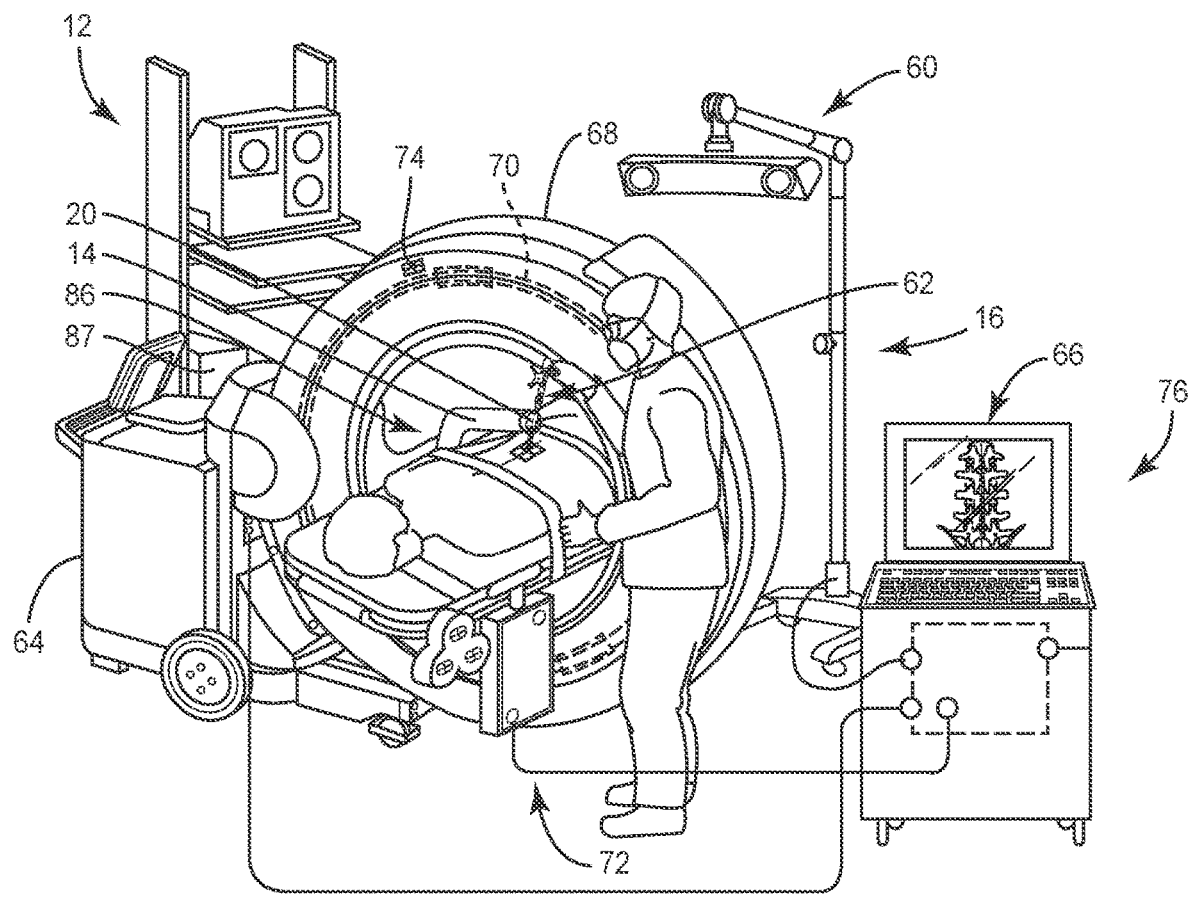
FIG. 1 is a plan view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises an image guided, robot assisted spinal implant system. In some embodiments, the present surgical system comprises a robotic guidance system and a selectively coupled bone screw system that allows for operating room assembly of a bone fastener. In some embodiments, the systems and methods of the present disclosure comprise surgical robotic guidance, surgical navigation and medical devices including surgical instruments and implants that are employed with a surgical treatment, as described herein, for example, with a cervical, thoracic, lumbar and/or sacral region of a spine.

In some embodiments, the present surgical system is employed with a method of performing robotically-assisted spinal surgery. In some embodiments, the method includes the step of delivering posterior spinal instrumentation through robotic-assisted trajectory alignment tools. In some embodiments, the present surgical system and method includes surgical robotic guidance having robotic software that performs registration of a patient anatomy to a three dimensional working space of a robot.

In some embodiments, the present surgical system is employed with a method of performing robotically-assisted spinal surgery including the step of generating a pre-operative CT scan that is used to pre-plan locations of pedicle screws for implant in an operating room. In some embodiments, during surgery, the method includes the step of identification of the same patient anatomy as recorded on the pre-operative CT scan. In some embodiments, the patient anatomy is accurately identified and located in the robot's three dimensional coordinate system to proceed with a selected procedure. In some embodiments, registration and placement of the pedicle screws is performed prior to spinal manipulation including decompression, disc preparation and/or interbody insertion, to avoid alteration of a patient's anatomy, for example, vertebral bones. Such alteration can prevent the robotic software from identifying common landmarks during an intra-operative registration process. In some embodiments, the present system and method avoid interference from implant receivers implanted prior to spinal manipulation.

In some embodiments, the present surgical system is employed with a method of performing robotically-assisted spinal surgery including the step of inserting screws that only have a shank-portion of a screw assembly when using robotic guidance. In some embodiments, after the screw shanks are placed under robotic guidance, decompression, disc preparation and/or interbody insertion can be performed without interference; for example, such interference can occur from screws with implant receivers implanted prior to spinal manipulation, which can interfere with access to a surgical site. In some embodiments, after decompression, disc preparation and/or interbody insertion, implant receivers, for example, modular implant receivers or screw heads may be attached to the screw shanks. In some embodiments, this configuration of the modular screw provides a screw shank having a smaller head/shaft diameter of an unassembled construct, relative to an assembled screw having an implant receiver, which uses robotic guidance for spinal fusion surgery.

In some embodiments, the present surgical system is employed with a method that includes the steps of placing a spinal construct having screw-shanks, for example, headless screws that will have modular heads attached thereafter and employed with a robotically-assisted trajectory system. In some embodiments, the present surgical system is employed with a method that includes the steps of registering a robot, placing screw shanks using a robotic trajectory guidance, performing decompression and disc removal, inserting interbody devices with vertebrae, connecting screw heads to the screw shanks, inserting spinal rods with the screw heads and securing the spinal construct with the vertebrae.

In some embodiments, the present surgical system comprises a driver configured for use with a modular screw platform. In some embodiments, the driver is configured for engagement with a screw shank, without a tulip head attached. In some embodiments, the driver includes a collet and a sleeve. In some embodiments, the sleeve is sized to grasp a spherical head of the screw shank. In some embodiments, the surgical system is utilized with a method including the step of disposing a driver in an initial open configuration by translating the sleeve out of engagement with the collet allowing the collet to expand for disposal of the screw shank. In some embodiments, the method includes the step of inserting the screw shank into the collet. In some embodiments, the method includes the step of engaging the screw shank with tissue. In some embodiments, the method includes the step of translating the sleeve out of engagement with the collet to release the screw shank. In some embodiments, the surgical instrument comprises a driver configured to be utilized with multiple design requirements of a modular screw platform. In some embodiments, the surgical instrument includes a driver configured to drive a bone screw shank without a tulip head attached thereto.

In some embodiments, the present surgical system comprises a modular system having a bone fastener including an array of members, such as, for example, receivers that can be selectively coupled to members, such as, for example, bone screw shafts. In some embodiments, the present surgical system comprises a selectively coupled bone fastener that can be assembled on a surgical table or in-situ. In some embodiments, the selectively coupled bone fastener is assembled with a force of less than 50 Newtons (N). In some embodiments, the bone fastener is selectively coupled with a non-instrumented assembly. In some embodiments, the non-instrumented assembly comprises manually engaging a screw shaft with a head/receiver of the bone fastener. In some embodiments, the non-instrumented assembly comprises manually engaging the screw shaft in a pop-on engagement with the head/receiver of the bone fastener. In some embodiments, a force required to manually engage a screw shaft with a head/receiver of the bone fastener in a non-instrumented assembly is in a range of 2 to 50 N. In some embodiments, a force required to manually engage a screw shaft with a head/receiver of the bone fastener in a non-instrumented assembly is in a range of 5 to 10 N. In some embodiments, a screw shaft is manually engaged with a head/receiver of the bone fastener in a non-instrumented assembly, as described herein, such that removal of the head/receiver from the screw shaft requires a force and/or a pull-out strength of at least 5000 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the bone fastener includes a ring disposed with a receiver connectable with a screw shaft. In some embodiments, the ring is configured to snap onto the screw shaft. In some embodiments, the ring has a minimized thickness and/or height to facilitate snapping the ring onto the screw shaft. In some embodiments, the force required to snap the ring onto the screw shaft is in a range of 2 to 50 N. In some embodiments, the force required to snap the ring onto the screw shaft is in a range of 5 to 10 N.

In some embodiments, the bone fastener is configured for assembly without the use of an instrument, such as, for example, a practitioner, surgeon and/or medical staff utilizes their hands for assembly. In some embodiments, the system requires minimal force to attach a receiver and a shaft in-situ thereby reducing a pre-load on the vertebrae, such as, for example, the pedicle. In some embodiments, the bone fastener includes a receiver having a double ring chamber. In some embodiments, the bone fastener includes an expandable ring. In some embodiments, the bone fastener is configured for assembly with the use of an instrument.

In some embodiments, the bone fastener includes an implant receiver that is rotatable and/or pivotable relative to a screw shaft in a selected range of movement configuration, for example, a multi-axial screw (MAS), a uni-axial screw (UAS), a fixed angle screw (FAS), a sagittal adjusting screw (SAS) or a transverse sagittal adjusting screw (TSAS). In some embodiments, the bone fastener can include one or more multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, fixation plates and/or posts.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical robotic guidance, surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Spinal implant system 10, as described herein, includes a surgical robotic guidance system 12 having a robotic arm 14, which is employed with a surgical navigation system 16 and one or a plurality of surgical instruments for manipulating vertebral tissue, and for delivering and introducing components of spinal constructs for engagement with the vertebral tissue. For example, a surgical driver 18 can be employed with an end effector 20 of robotic arm 14 to facilitate implant with robotic arm 14. Driver 18 is guided through end effector 20 for guide-wireless insertion of a spinal implant, such as, for example, a screw shaft 22 of a bone fastener 24.

Screw shaft 22 includes an interchangeable mating element, such as, for example, a head 26 that is interchangeable with a mating element, as described herein, of a receiver 28 to form a selected bone fastener 24 having a selected movement of its components parts and/or movement relative to vertebral tissue. In some embodiments, the selected movement includes rotation and/or pivotal movement of shaft 22 relative to receiver 28 about one or a plurality of axes. In some embodiments, the selected movement includes rotation and/or pivotal movement of shaft 22 relative to receiver 28 through one or a plurality of planes. In some embodiments, shaft 22 is connected to a selected receiver 28 to comprise a MAS, UAS, FAS, SAS or TSAS. In some embodiments, spinal implant system 10 comprises a spinal implant kit, which includes receivers 28 and alternate receivers, such as those described herein. A selected receiver 28 is configured for selection from the kit of receivers 28 such that the selected receiver 28 is connectable with an interchangeable shaft 22. In some embodiments, a selected receiver 28 is configured for selection from the kit of receivers 28 such that receiver 28 is connectable with a compatible shaft 22.

Shaft 22 has a cylindrical cross-sectional configuration and includes an outer surface having an external thread form. In some embodiments, the external thread form may include a single thread or a plurality of discrete threads. In some embodiments, other engaging structures may be located on shaft 22, such as, for example, a nail configuration, barbs, expanding elements, raised elements and/or spikes to facilitate engagement of shaft 22 with tissue. In some embodiments, all or only a portion of shaft 22 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 22 may include one or a plurality of openings. In some embodiments, all or only a portion of the outer surface of shaft 22 may have alternate surface configurations to enhance fixation with tissue, such as, for example, rough, arcuate, undulating, mesh, porous, semi-porous, dimpled and/or textured. In some embodiments, all or only a portion of shaft 22 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 22 may be cannulated.

Head 26 defines a drive interface, such as, for example, a socket 30. Socket 30 is configured for a mating engagement with driver 18 and defines a hexalobe configuration. Driver 18 includes an inner drive 32 engageable with socket 30 of head 26 and an outer sleeve 34 to dispose driver 18 in a capture orientation of screw shaft 22. In some embodiments, sleeve 34/drive 32 define a cavity configured for disposal of head 26 and sleeve 34 includes an expandable collet to capture shaft 22. In some embodiments, sleeve 34/drive 32 define a cavity configured for disposal of head 26 and sleeve 34 includes a threaded portion (not shown) configured for engagement with a portion of head 26 to pull and/or draw shaft 22 axially into the cavity and into engagement with drive 32 to capture shaft 22.

Figure 16:
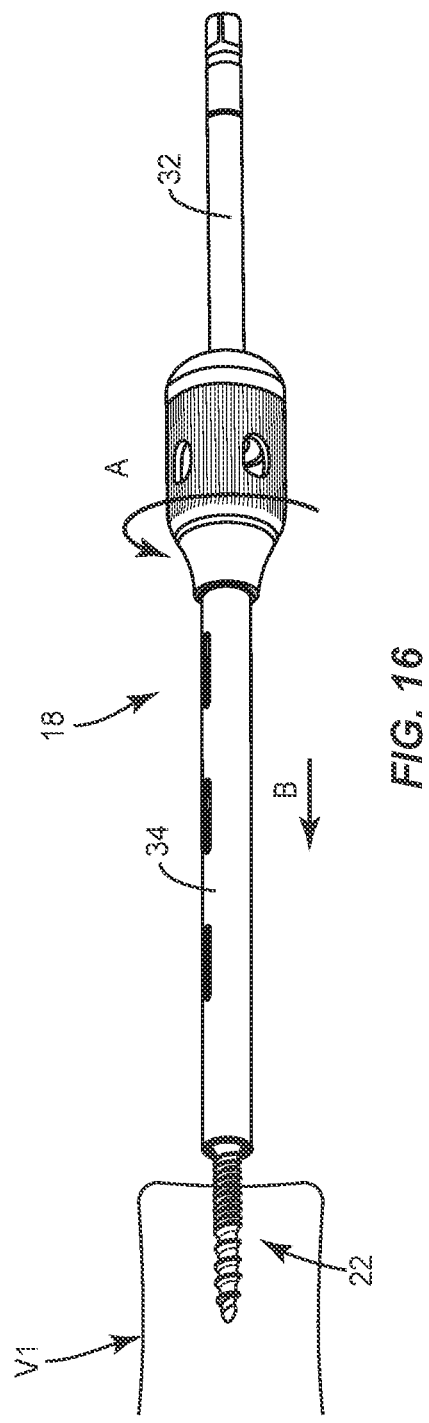
FIG. 16 is a perspective view of components of one embodiment of a surgical system in accordance with the principles of the present disclosure disposed with vertebrae.
Figure 17:
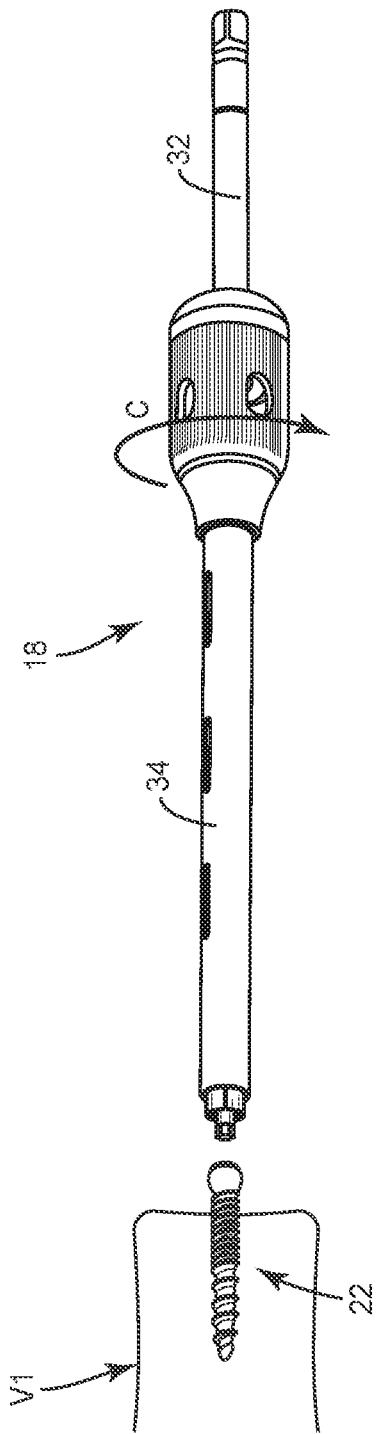
FIG. 17 is a perspective view of components of one embodiment of a surgical system in accordance with the principles of the present disclosure disposed with vertebrae.

For example, in use, driver 18 is disposed in an open orientation, such that drive 32 extends from driver 18, as shown in FIG. 16. Drive 32 is aligned with socket 30 and engaged with head 26. Sleeve 34 is rotated relative to drive 32 in a clockwise direction, as shown by arrow A in FIG. 16, such that internal threaded surfaces (not shown) cause sleeve 34 to axially translate, as shown by arrow B in FIG. 16, relative to drive 32 to capture shaft 22 with drive 32. Upon connection and capture of shaft 22, driver 18 is rotated in a clockwise direction, as shown by arrow A in FIG. 16, such that driver 18 is engaged with shaft 22 to manipulate, fasten, drive, torque or insert shaft 22 with tissue, similar to that described herein. To release driver 18 from shaft 22, sleeve 34 is rotated relative to drive 32, in a counter-clockwise direction, as shown by arrow C in FIG. 17, such that sleeve 34 axially translates relative to drive 32 to release head 26 from drive 32. Driver 18 is disengageable from shaft 22.

In some embodiments, upon disposal of shaft 22 with vertebral tissue, as described herein, receiver 28 includes a mating surface 40 configured to interface in a selective mating engagement with head 26. In some embodiments, mating surface 40 includes flats and/or arcuate surfaces to form various bone screw configurations, such as those described herein. Head 26 is slidably engageable with surface 40 and movable relative thereto such that shaft 22 is rotatable along a plurality of axes relative to receiver 28 including rotation about axis X1. As such, interchangeable shaft 22 is connected with a selected receiver 28 from the kit of receivers 28 to form a bone fastener 24.

Receiver 28 defines a groove 42 configured for disposal of a circumferential ring 44, as shown in FIGS. 5-9. Groove 42 includes a circumferential channel 46 having a diameter d1 and a circumferential channel 48 having a diameter d2 that is greater than diameter d1. Channel 48 is adjacent and proximal to channel 46. Channel 48 is separated from channel 46 by a lip 50. In some embodiments, shaft 22 is manually engageable with receiver 28 and/or shaft 22 is coupled with receiver 28 in a non-instrumented assembly such that ring 44 translates from and into channels 46, 48, and over lip 50, as described herein. Ring 44 is expandable and resilient between a contracted and/or capture orientation, and an expanded orientation, as described herein. Ring 44 facilitates manual engagement of a selected receiver 28 and shaft 22 such that the selected receiver 28 is attached with shaft 22 in a non-instrumented assembly, as described herein.

In some embodiments, manual engagement and/or non-instrumented assembly of receiver 28 and shaft 22 includes the coupling of receiver 28 and shaft 22 without use of separate and/or independent instrumentation engaged with bone fastener 24 components to effect assembly. In some embodiments, manual engagement and/or non-instrumented assembly includes a practitioner, surgeon and/or medical staff grasping receiver 28 and shaft 22 and forcibly assembling the components of bone fastener 24. In some embodiments, manual engagement and/or non-instrumented assembly includes a practitioner, surgeon and/or medical staff grasping receiver 28 and shaft 22 and forcibly snap fitting the components of bone fastener 24 together, as described herein. In some embodiments, manual engagement and/or non-instrumented assembly includes a practitioner, surgeon and/or medical staff grasping receiver 28 and shaft 22 and forcibly pop fitting the components of bone fastener 24 together and/or pop fitting receiver 28 onto shaft 22, as described herein. In some embodiments, a force in a range of 2-50 N is required to manually engage receiver 28 and shaft 22 and forcibly assemble the components of bone fastener 24. For example, a force in a range of 2-50 N is required to snap fit and/or pop fit assemble receiver 28 and shaft 22. In some embodiments, a force in a range of 5-10 N is required to manually engage receiver 28 and shaft 22 and forcibly assemble the components of bone fastener 24. For example, a force in a range of 5-10 N is required to snap fit and/or pop fit assemble receiver 28 and shaft 22. In some embodiments, shaft 22 is manually engaged with receiver 28 in a non-instrumented assembly, as described herein, such that removal of receiver 28 from shaft 22 requires a force and/or a pull-out strength of at least 5000 N. In some embodiments, this configuration provides manually engageable components of bone fastener 24 that are assembled without instrumentation, and subsequent to assembly, the assembled components have a selected pull-out strength and/or can be pulled apart, removed and/or separated with a minimum required force. In some embodiments, bone fastener 24 is configured for assembly with the use of an instrument.

Receiver 28 includes a slot 52 configured to receive a flange of a crown 54. Crown 54 is configured for disposal within an implant cavity 56 of receiver 28 and disposal of a spinal rod (not shown). Head 26 is interchangeably engageable with any of the plurality of receivers 28. Head 26 includes a substantially spherical proximal portion configured for moveable disposal with the selected receiver 28 and crown 54. Head 26 includes a plurality of ridges to improve purchase with crown 54. Head 26 has a maximum diameter d3 and applies a force to ring 44 to move ring 44 between a contracted and/or capture orientation and an expanded orientation, as described herein. In some embodiments, head 26 includes interchangeable mating surfaces, such as for example, arcuate portions and/or planar portions configured for disposal with receiver 28 to limit rotation of receiver 28 relative to shaft 22. In some embodiments, receiver 28 may be disposed with shaft 22 in alternate fixation configurations, such as, for example, friction fit, pressure fit, locking protrusion/recess, locking keyway and/or adhesive.

Figure 9:
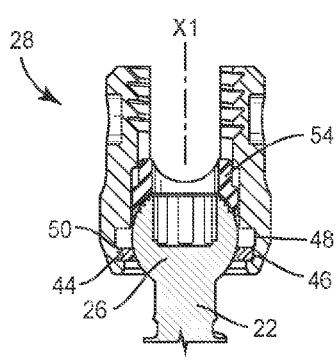
FIG. 9 is a side view of the components shown in FIG. 5.

Receiver 28 extends along and defines an axis X1, as shown in FIG. 9. Receiver 28 includes a pair of spaced apart arms that define implant cavity 56 therebetween configured for disposal of a component of a spinal construct, such as, for example, a spinal rod (not shown). The arms of receiver 28 each extend parallel to axis X1. In some embodiments, the arms may be disposed at alternate orientations, relative to axis X1, such as, for example, transverse, perpendicular and/or other angular orientations such as acute or obtuse, coaxial and/or may be offset or staggered. The arms of receiver 28 each include an arcuate outer surface extending between a pair of side surfaces. At least one of the outer surfaces and the side surfaces of the arms of receiver 28 have at least one recess or cavity therein configured to receive an insertion tool, compression instrument and/or instruments for inserting and tensioning bone fastener 24. In some embodiments, the arms of receiver 28 are connected at proximal and distal ends thereof such that receiver 28 defines a closed spinal rod slot.

Cavity 56 is substantially U-shaped. In some embodiments, all or only a portion of cavity 56 may have alternate cross section configurations, such as, for example, closed, V-shaped, W-shaped, oval, oblong triangular, square, polygonal, irregular, uniform, non-uniform, offset, staggered, and/or tapered. Receiver 28 includes an inner surface having thread forms configured for engagement with a coupling member, such as, for example, a setscrew (not shown), to retain a spinal construct, such as, for example, a spinal rod (not shown) within cavity 56. In some embodiments, receiver 28 may be disposed with the coupling member in alternate fixation configurations, such as, for example, friction fit, pressure fit, locking protrusion/recess, locking keyway and/or adhesive. In some embodiments, receiver 28 may include alternate configurations, such as, for example, closed, open and/or side access.

Figure 2:
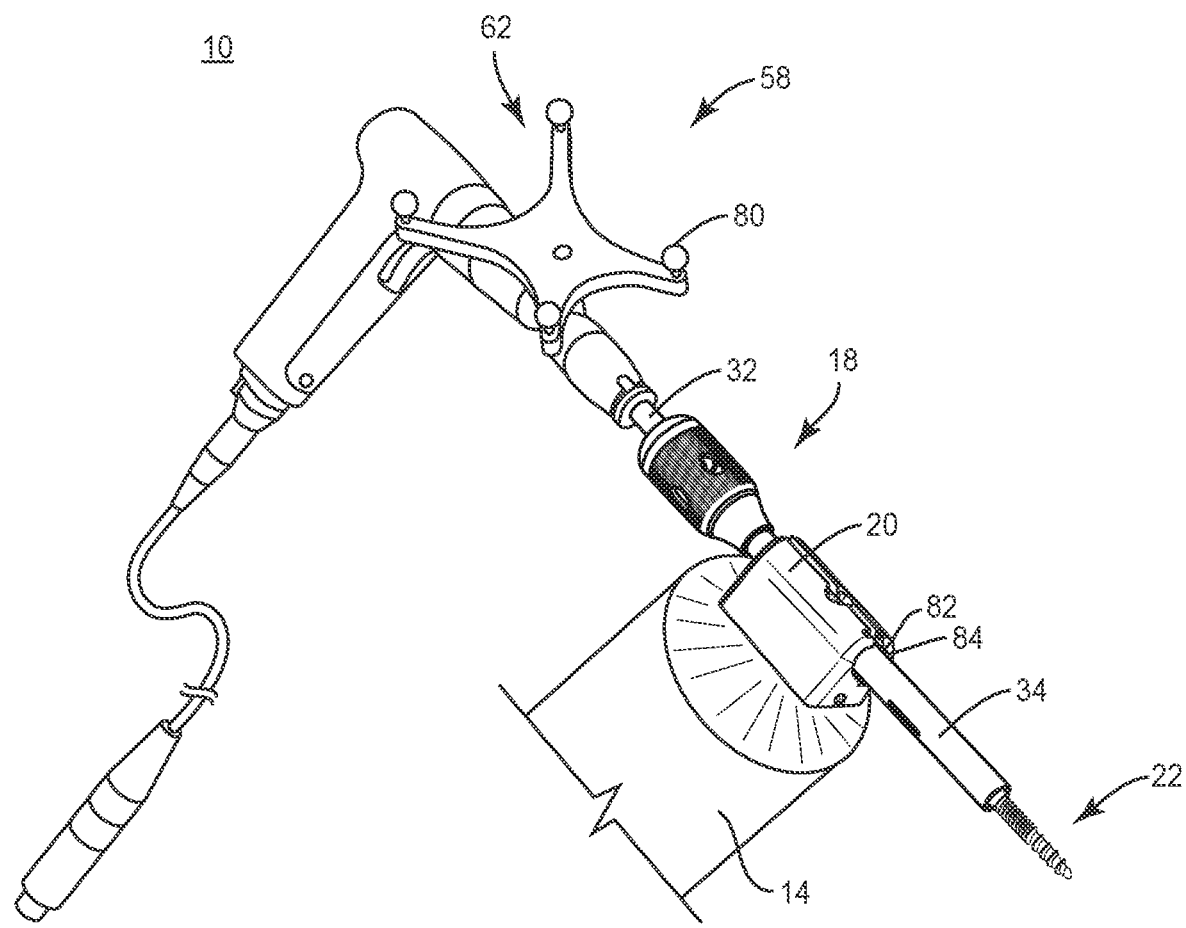
FIG. 2 is a perspective view of components of one embodiment of a surgical system in accordance with the principles of the present disclosure.
Figure 3:
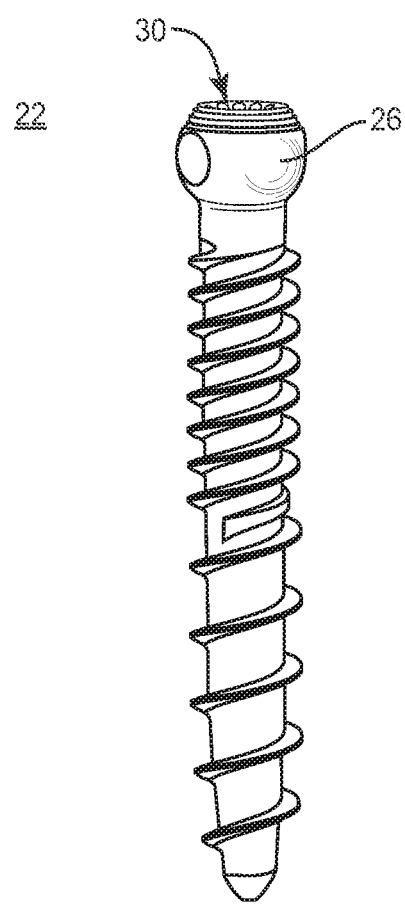
FIG. 3 is a side view of components of one embodiment of a surgical system in accordance with the principles of the present disclosure.
Figure 4:
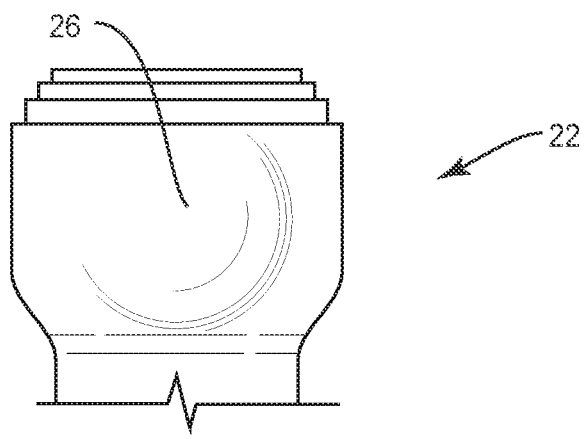
FIG. 4 is a break away view of the components shown in FIG. 3.

In some embodiments, driver 18 includes a navigation component 58, as shown in FIG. 2. Driver 18 is configured for disposal adjacent a surgical site such that navigation component 58 is oriented relative to a sensor array 60, as shown in FIG. 1, to facilitate communication between navigation component 58 and sensor array 60 during a surgical procedure, as described herein. Navigation component 58 is configured to generate a signal representative of a position of screw shaft 22 relative to driver 18 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 58 is connected with driver 18 via an integral connection, friction fit, pressure fit, interlocking engagement, mating engagement, dovetail connection, clips, barbs, tongue in groove, threaded, magnetic, key/keyslot and/or drill chuck.

Navigation component 58 includes an emitter array 62. Emitter array 62 is configured for generating a signal to sensor array 60 of surgical navigation system 16. In some embodiments, the signal generated by emitter array 62 represents a position of screw shaft 22 relative to driver 18 and relative to tissue, such as, for example, bone. In some embodiments, the signal generated by emitter array 62 represents a three-dimensional position of screw shaft 22 relative to tissue. In some embodiments, emitter array 62 may include a reflector array configured to reflect a signal from sensor array 60.

In some embodiments, sensor array 60 receives signals from emitter array 62 to provide a three-dimensional spatial position and/or a trajectory of screw shaft 22 relative to driver 18 and/or tissue. Emitter array 62 communicates with a processor of a computer 64 of navigation system 16 to generate data for display of an image on a monitor 66, as described herein. In some embodiments, sensor array 60 receives signals from emitter array 62 to provide a visual representation of a position of screw shaft 22 relative to driver 18 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 16 is configured for acquiring and displaying medical imaging, such as, for example, x-ray images appropriate for a given surgical procedure. In some embodiments, pre-acquired images of a patient are collected. In some embodiments, surgical navigation system 16 can include an O-arm® imaging device 68 sold by Medtronic Navigation, Inc. having a place of business in Louisville, Colo., USA. Imaging device 68 may have a generally annular gantry housing that encloses an image capturing portion 70.

In some embodiments, navigation system 16 comprises image capturing portion 70 that may include an x-ray source or emission portion and an x-ray receiving or image receiving portion located generally or as practically possible 180 degrees from each other and mounted on a rotor (not shown) relative to a track of image capturing portion 70. Image capturing portion 70 can be operable to rotate 360 degrees during image acquisition. Image capturing portion 70 may rotate around a central point or axis, allowing image data of the patient to be acquired from multiple directions or in multiple planes. Surgical navigation system 16 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 16 can include C-arm fluoroscopic imaging systems, which can generate three-dimensional views of a patient. The position of image capturing portion 70 can be precisely known relative to any other portion of an imaging device of navigation system 16. In some embodiments, a precise knowledge of the position of image capturing portion 70 can be used in conjunction with a tracking system 72 to determine the position of image capturing portion 70 and the image data relative to the patient.

Tracking system 72 can include various portions that are associated or included with surgical navigation system 16. In some embodiments, tracking system 72 can also include a plurality of types of tracking systems, such as, for example, an optical tracking system that includes an optical localizer, such as, for example, sensor array 60 and/or an EM tracking system that can include an EM localizer. Various tracking devices can be tracked with tracking system 72 and the information can be used by surgical navigation system 16 to allow for a display of a position of an item, such as, for example, a patient tracking device, an imaging device tracking device 74, and an instrument tracking device, such as, for example, emitter array 62, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to computer 64 where they may be forwarded to a computer 76. Image transfer may be performed over a standard video connection or a digital link including wired and wireless. Computer 76 provides the ability to display, via monitor 66, as well as save, digitally manipulate, or print a hard copy of the received images. In some embodiments, images may also be displayed to the surgeon through a heads-up display.

In some embodiments, surgical navigation system 16 provides for real-time tracking of the position of screw shaft 22 relative to driver 18 and/or tissue can be tracked. Sensor array 60 is located in such a manner to provide a clear line of sight with emitter array 62, as described herein. In some embodiments, fiducial markers 80 of emitter array 62 communicate with sensor array 60 via infrared technology. Sensor array 60 is coupled to computer 64, which may be programmed with software modules that analyze signals transmitted by sensor array 60 to determine the position of each object in a detector space.

Driver 18 is configured for use with end effector 20. End effector 20 includes a surface 82 that defines a channel 84. Channel 84 is configured for passage of the components of bone fastener 24 and disposal of driver 18, and/or spinal construct components and surgical instruments, as described herein. Robotic arm 14 includes position sensors (not shown), similar to those referenced herein, which measure, sample, capture and/or identify positional data points of end effector 20 in three dimensional space for a guide-wireless insertion of components of bone fasteners 24, for example, screw shafts 22 with selected vertebral levels. In some embodiments, surface 82 comprises an axial trajectory guide configured for passage of the components of bone fastener 24 and disposal of driver 18, and/or spinal construct components and surgical instruments, as described herein. In some embodiments, a sleeve, which comprises an axial trajectory guide, is connected with surface 82. In some embodiments, the position sensors of robotic arm 14 are employed in connection with surgical navigation system 16 to measure, sample, capture and/or identify positional data points of end effector 20 in connection with surgical treatment, as described herein. The position sensors are mounted with robotic arm 14 and calibrated to measure positional data points of end effector 20 in three dimensional space, which are communicated to the components of surgical robotic guidance system 12 and/or computer 64. See, for example, the surgical robotic guidance systems and methods described in U.S. Pat. No. 8,571,638, the contents of which being hereby incorporated by reference herein in its entirety.

Surgical robotic guidance system 12 includes a surgical robot 86 including robotic arm 14, which positions one or more surgical instruments, as described herein, with respect to a surgical site and is employed with a method for using robot 86 to assist in surgical procedures. In some embodiments, robot 86 attaches to patient anatomy, for example, bone with a clamp (not shown) or K-wires of robot 86. Robotic arm 14 extends and moves relative to a base of robot 86 to assist in surgical procedures. See, for example, the surgical robot configurations described in U.S. Pat. No. 8,571,638, the contents of which being hereby incorporated by reference herein in its entirety. In some embodiments, robot 86 is not physically connected with the patient anatomy, for example, a navigation system, as described herein, registers the patient anatomy with respect to the location of robot 86, which includes the location of the robot's end effector 20, such that robotic arm 14 extends and moves relative to a base of robot 86 to assist in surgical procedures.

In some embodiments, surgical robotic guidance system 12 includes a control unit 87 that matches data from CT scans and C-arm images to locate surgical robot 86 and allows a surgeon to control surgical robot 86, through the use of a mouse, joystick, touch screen, or the like; and monitor 66. In some embodiments, control unit 87 may include a central processing unit (CPU) and user interface communicating with monitor 66 and surgical robot 86. Surgical robot 86 aligns end effector 20 and drive 18 for alignment with a surgical site requiring a surgical procedure percutaneously, mini-open or in open procedures.

In one embodiment, as shown in FIGS. 9-12, spinal implant system 10, similar to the systems and methods described herein, is employed in connection with one or more surgical procedures, as described herein. Initially, spinal implant system 10 is employed with a method for treating a spine that includes a preparation and/or a pre-operative step 400. Preparation step 400 includes imaging a patient anatomy, for example, pre-operatively generating three dimensional images of the patient anatomy. In some embodiments, preparation step 400 includes performing a three-dimensional scan in an imaging step 410, for example, a CT scan or MRI scan, of the patient anatomy, for example, the spine. In some embodiments, preparation step 400 may include verification of surgical instruments, draping and/or camera positioning. In some embodiments, the preparation step includes utilizing O-Arm® imaging device 68 in the operating room to obtain the three-dimensional images of the patient anatomy intra-operatively and/or prior to surgery 700.

Figure 11:
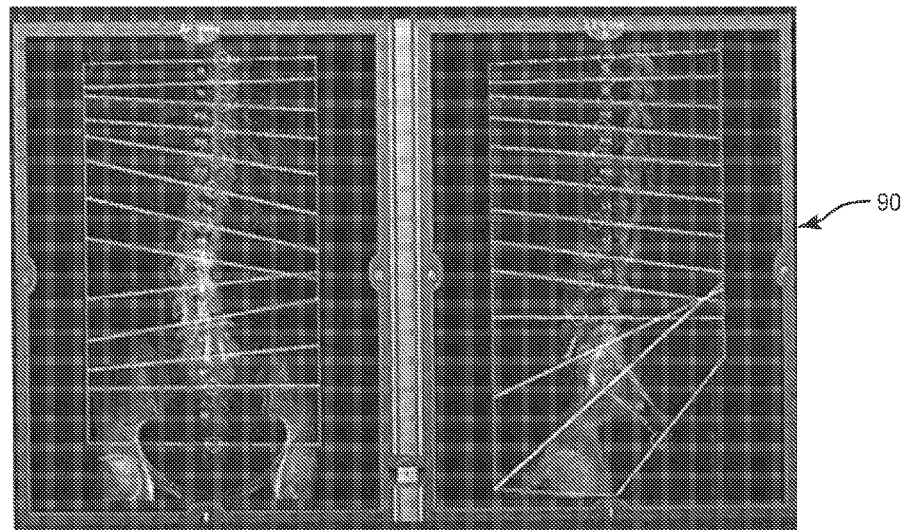
FIG. 11 is a graphical representation of components of one embodiment of a surgical system in accordance with the principles of the present disclosure.
Figure 12:
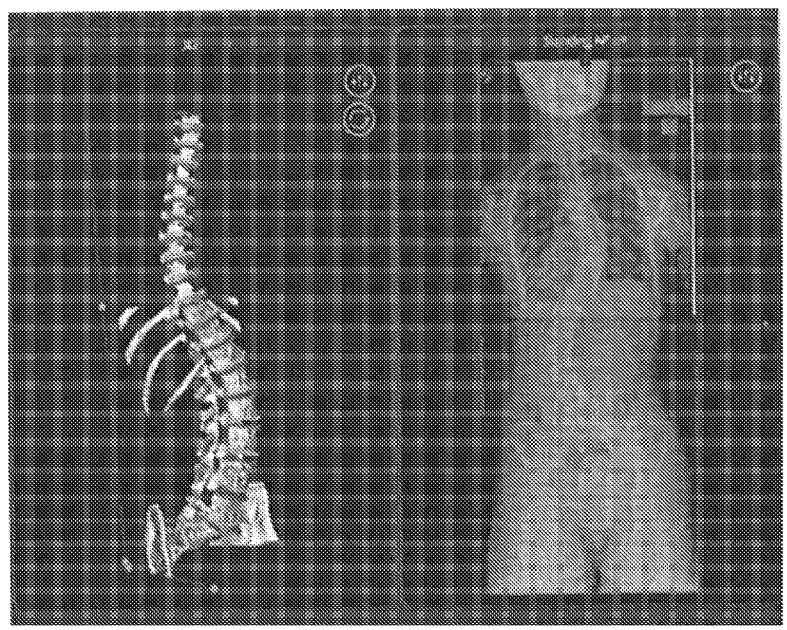
FIG. 12 is a graphical representation of components of one embodiment of a surgical system in accordance with the principles of the present disclosure.

A surgeon reviews three-dimensional scan 410 and formulates and selects an implant strategy 420 for the components of a spinal construct with the patient anatomy according to three-dimensional scan 410. In some embodiments, implant strategy 420 includes preparing a pre-operative surgical plan based on three-dimensional scan 410. In some embodiments, implant strategy 420 includes selecting an insertion path, for example, screw trajectory of screw shaft 22 and positioning of screw shaft 22 with the vertebral tissue. In some embodiments, implant strategy 420 includes selecting a plurality of screw trajectories for positioning a plurality of screw shafts 22 with vertebrae of the patient anatomy. In some embodiments, implant strategy 420 employs pre-operative analytics software including anatomy recognition and vertebral segmentation algorithms for surgical visualization based on a patient's images, for example as shown in FIGS. 11 and 12, which facilitates formulating implant strategy 420 including implant and trajectory placement planning. In some embodiments, implant strategy 420 may be created pre-operatively or intra-operatively. Implant strategy 420 includes surgical parameters of trajectory and positioning of one or more implants, which are communicated to surgical robotic guidance system 12 to direct robot 86 to a location where a surgical procedure is to be performed to assist in surgical procedures.

In some embodiments, a calibration imaging step 500 includes making an incision in the patient at a site where a connecting member, such as, for example, a clamp or a pin (not shown) of robot 86 is attached to a selected portion of the patient anatomy, such as, for example, vertebra in a step 510. In some embodiments, the clamp is attached with a pelvis, sacrum or ilium of the patient. The clamp is configured to secure robot 86 with the patient. The clamp stabilizes robot 86 with the patient to resist and/or prevent relative movement. In some embodiments, the clamp includes an emitter or reflector array to communicate a signal to sensor array 60. In some embodiments, calibration imaging step 500 includes robot 86 not being physically connected with the patient anatomy. For example, surgical navigation system 16 registers the patient anatomy, as described herein, relative to the location of robot 86, which includes the location of the robot's end effector 20, such that robotic arm 14 extends and moves relative to a base of robot 86 to assist in surgical procedures. The patient anatomy and robot 86 may each have reference markers, similar to those described herein, which are visible by surgical navigation system 16. This, in combination with imaging of the patient anatomy, as described herein and stored with surgical robotic guidance system 12 and/surgical navigation system 16, enables registering the patient's anatomy with respect to location of robot 86.

Figure 10A:
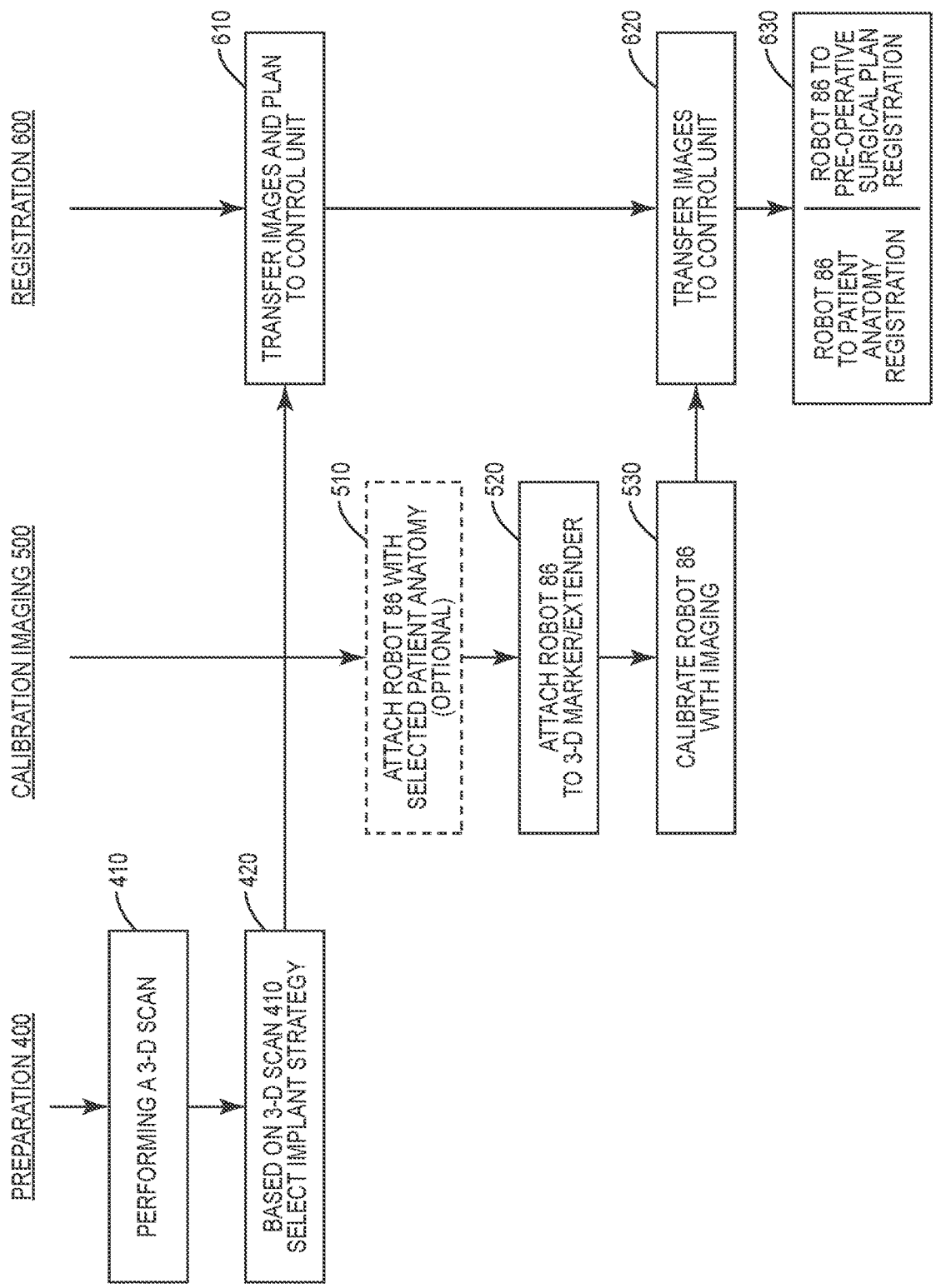
FIGS. 10A and 10B are flow diagrams illustrating representative steps of embodiments of a method and a surgical system in accordance with the principles of the present disclosure.
Figure 10B:
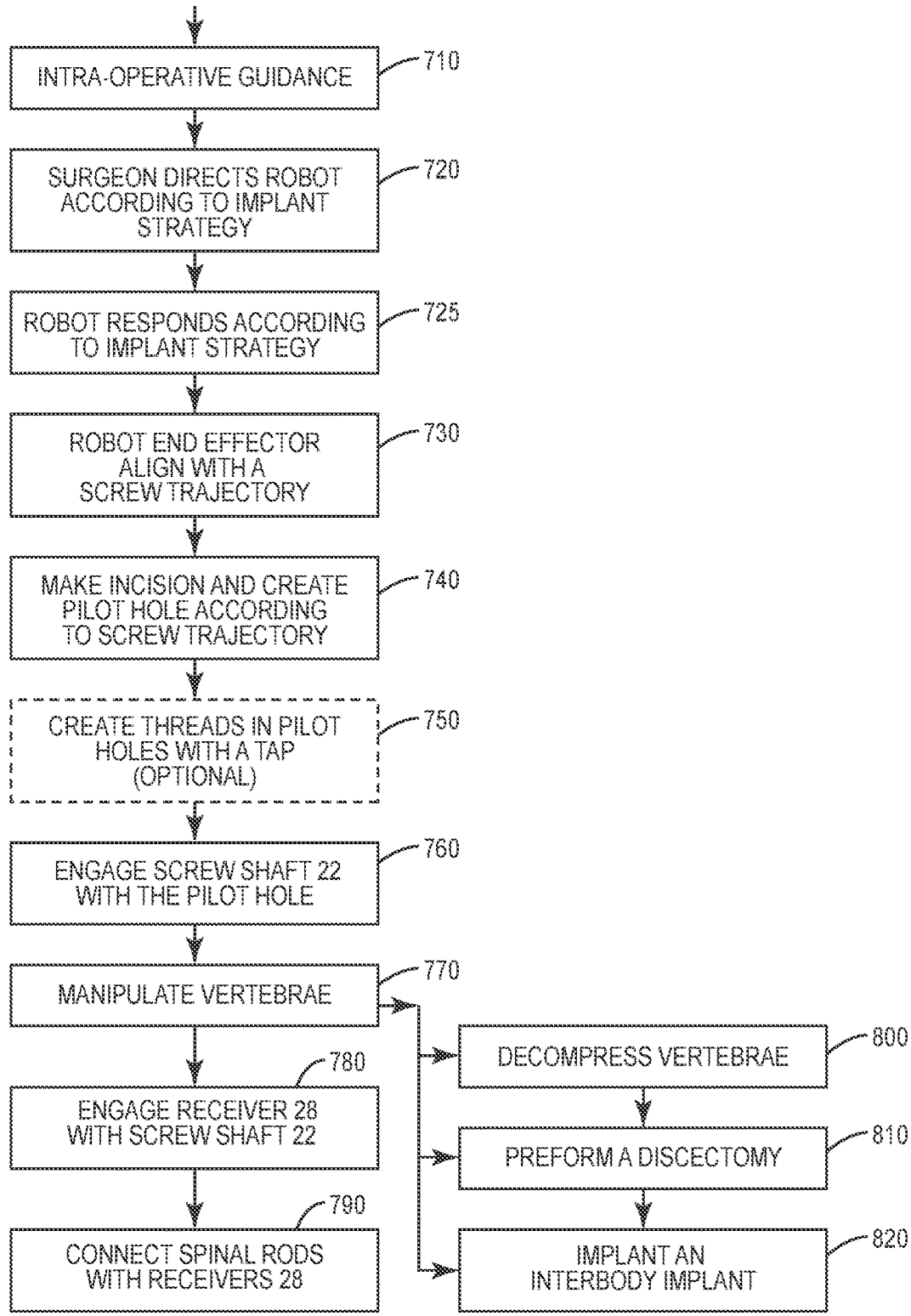
Figure 10C:
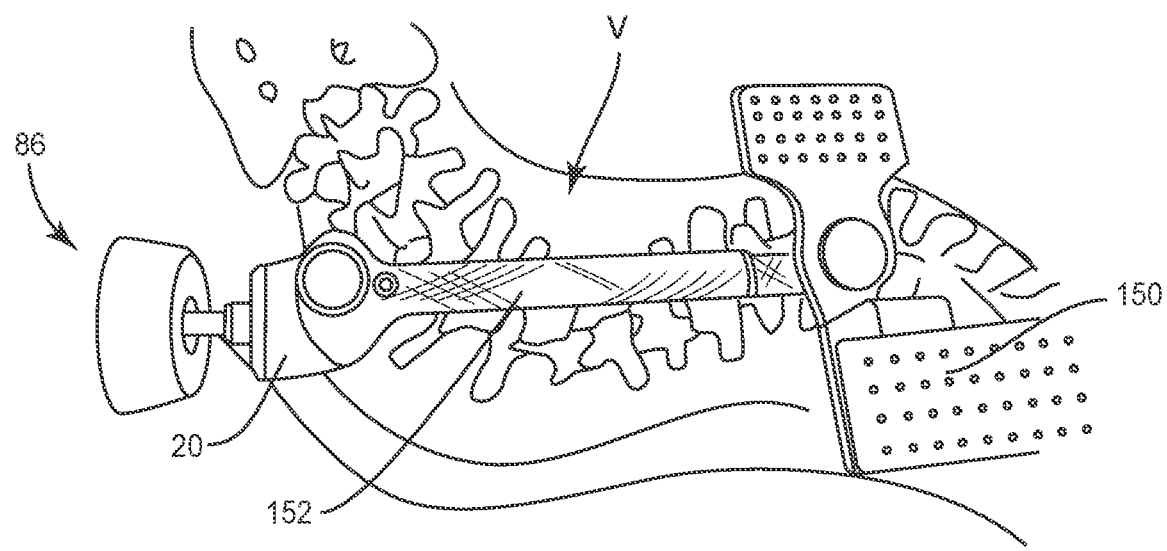
FIG. 10C is a plan view of components of one embodiment of a surgical system in accordance with the principles of the present disclosure.

A calibration step 520 includes attaching a 3D marker 150 and a target extender 152 with end effector 20 of robot 86, as shown in FIG. 10C. In some embodiments, robot 86 includes marker 150 and/or extender 152. Robot 86 is calibrated in a step 530 by obtaining imaging of the selected vertebra of the patient on the table in the operating room. In some embodiments, the images include taking C-arm images of the patient anatomy and these images are calibrated such that a three-dimensional image of the selected vertebra is generated. In some embodiments, fluoroscopic images are taken from different angles, such as, 0, 45, and 90 degrees. In some embodiments, multiple C-arm images are taken.

During a registration process 600, the three-dimensional scans 410 from preparation step 400 are transferred in a step 610 to control unit 87. The C-arm images from step 530 are transferred in a step 620 to control unit 87. A pseudo three-dimensional image of the selected vertebra is generated in a robot 86 to patient anatomy registration 630. In some embodiments, registration 630 includes robot 86 not being physically connected with the patient anatomy, as described herein. The three-dimensional scan 410 is matched with the multiple C-arm images in a robot 86 to the pre-operative surgical plan registration 630. See, for example, the registration systems and methods, as described in U.S. Pat. No. 8,571,638, the contents of which being hereby incorporated by reference herein in its entirety. Robot 86 is located adjacent to the selected vertebra in a three-dimensional image and can be manipulated by the surgeon according to implant strategy 420 for insertion of surgical tools, medical devices, or implants with a surgical site. Robot 86 can be controlled from control unit 87 and/or computers 64, 76.

In some embodiments, registration is accomplished by taking windows 90 of images of a surgical site, as shown in FIGS. 11 and 12. In some embodiments, windows 90 are selected that specifically relate to the known location of robot 86. Windows 90 are selected from the C-arm (fluoroscopic) image data. In some embodiments, the same windows are chosen from both the pseudo three-dimensional hybrid C-arm image and from the CT image (3D image).

During a surgery 700, surgical robotic guidance system 12 includes intra-operative guidance 710 such that a surgeon directs robot 86, in a step 720, to guide surgical instruments, as described herein, and implants at a trajectory and position according to implant strategy 420. Robot 86 responds, in a step 725, and moves end effector 20, which includes an axial trajectory guide, for example, channel 84 and/or a sleeve disposed with surface 82, into position, such that a spinal construct component and/or surgical instrument disposed with end effector 20 can be aligned with a location according to implant strategy 420. In some embodiments, the surgeon can insert a spinal construct component and/or surgical instrument with end effector 20 and visually verify positioning of the spinal construct component and/or surgical instrument from control unit 87 and/or monitor 66. In some embodiments, a surgeon can manipulate robot 86 by use of a joystick, mouse and/or touch screen.

The components of spinal implant system 10 can be employed with surgery 700 for treatment of an applicable condition or injury of an affected section of a spinal column and adjacent areas within a body, such as, for example, vertebrae V. To treat a selected section of vertebrae V, a medical practitioner obtains access to a surgical site including vertebrae V in any appropriate manner, such as through incision and retraction of tissues. In some embodiments, the components of spinal implant system 10 can be used in any existing surgical method or technique including open surgery, mini-open surgery, minimally invasive surgery and/or percutaneous surgical implantation, whereby vertebrae V are accessed through a mini-incision, or sleeve that provides a protected passageway to the area. Once access to the surgical site is obtained, the particular surgical procedure can be performed for treating the spine disorder.

Channel 84 of end effector 20 provides an axial guide for spinal construct components and/or surgical instruments according to implant strategy 420 and/or a surgical pathway for delivery of components of spinal implant system 10, which may include, such as, for example, drivers, extenders, reducers, spreaders, distracters, blades, clamps, forceps, elevators and drills, which may be alternately sized and dimensioned, and arranged as a kit. In some embodiments, the surgeon disposes a sleeve (not shown) with end effector 20, which provides an axial guide.

Figure 13:
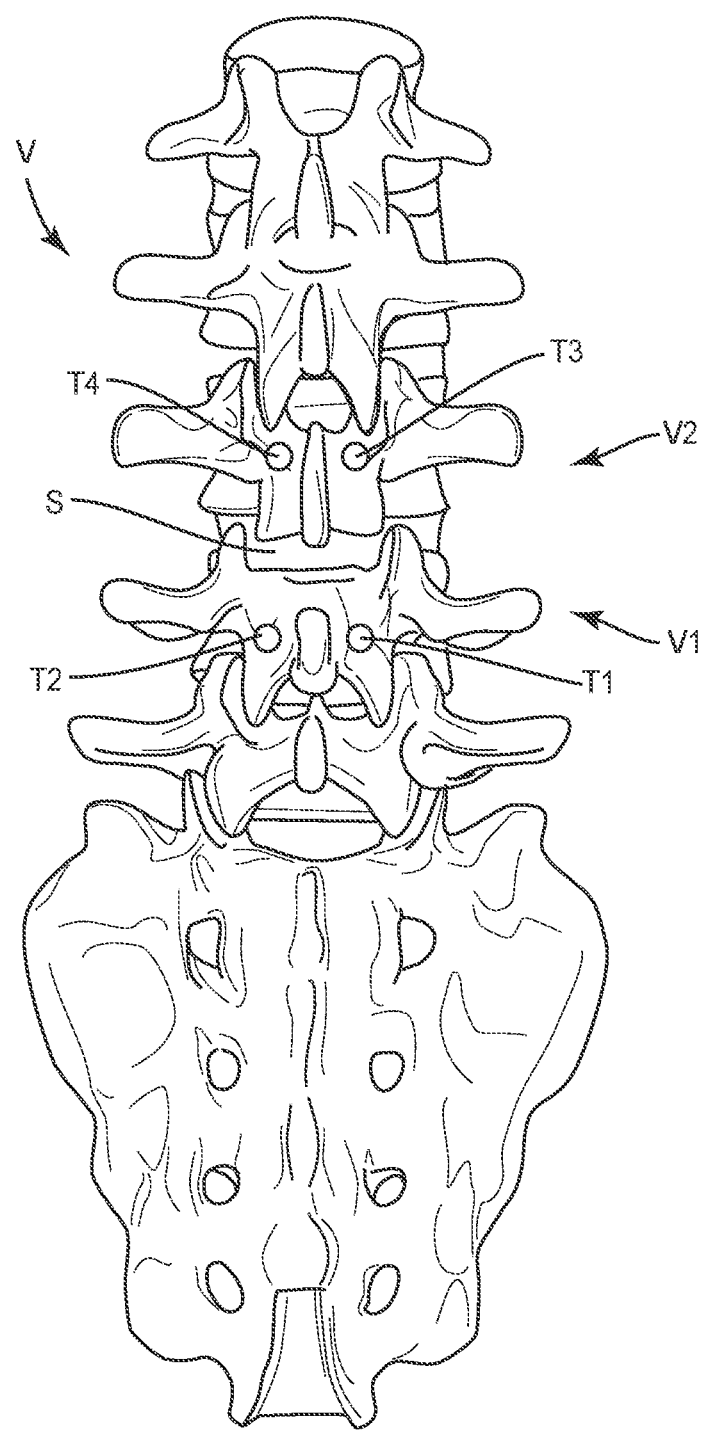
FIG. 13 is a plan view of one embodiment of an implant strategy in accordance with the principles of the present disclosure.

For example, implant strategy 420 includes a screw trajectory T1 of an insertion path and positioning of a screw shaft 22 with a lateral side of a vertebra V1, as shown in FIG. 13. Screw trajectory T1 includes an axial or linear pathway for delivering spinal construct components and/or surgical instruments to a selected location of the lateral side of vertebra V1, according to implant strategy 420.

During surgery 700, in a step 730, the surgeon moves arm 14 such that channel 84 is aligned with screw trajectory T1. In some embodiments, channel 84 and/or a sleeve, cannula and/or dilator disposed with channel 84 defines a surgical pathway along screw trajectory T1 to vertebra V1 In some embodiments, surface 82 of end effector 20 may be connected, attached or monolithically formed with a sleeve, cannula and/or dilator to define the surgical pathway along screw trajectory T1 to vertebra V1.

In a step 740, with channel 84 oriented along screw trajectory T1, the surgeon positions a cutting instrument (not shown) within the surgical pathway of channel 84. The cutting instrument is translated by the surgeon through channel 84 in alignment with screw trajectory T1 and creates an incision and the surgical pathway through tissue to vertebra V1. The surgeon removes the cutting instrument from channel 84. Alignment of channel 84 with screw trajectory T1 is maintained and the surgeon positions a drill (not shown) within the surgical pathway of channel 84. The drill is translated by the surgeon through the surgical pathway of channel 84 in alignment with screw trajectory T1. In some embodiments, a cannula or a drill guide is disposed with channel 84 to protect tissue and facilitate insertion and guidance of the drill. The drill is actuated to create a pilot hole in vertebra V1 along screw trajectory T1. The drill is removed from the surgical pathway of channel 84.

Figure 14:
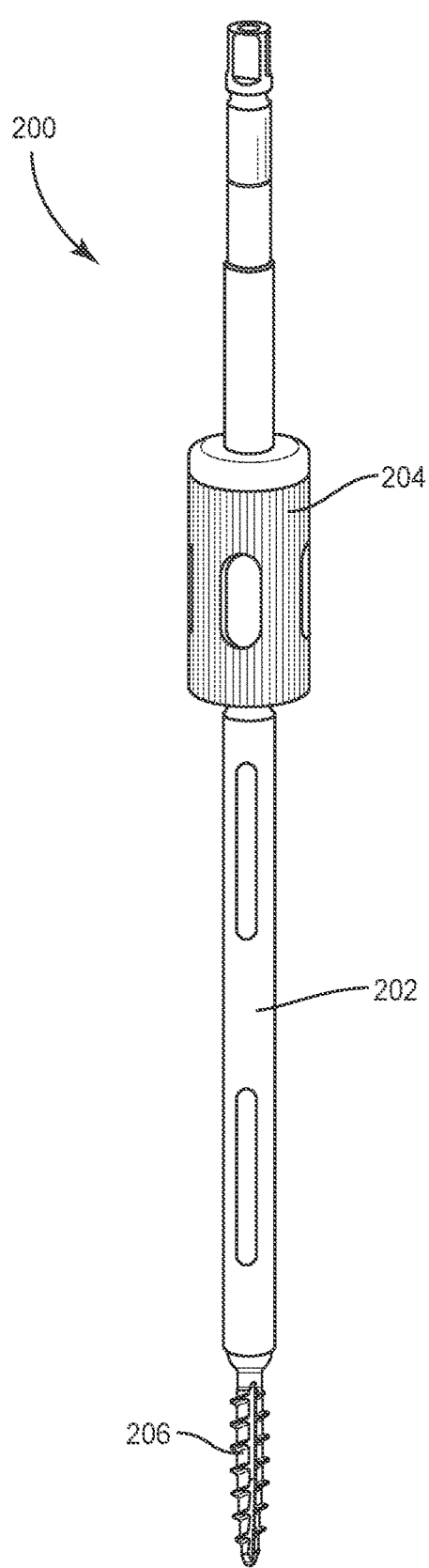
FIG. 14 is a perspective view of components of one embodiment of a surgical system in accordance with the principles of the present disclosure.
Figure 15:
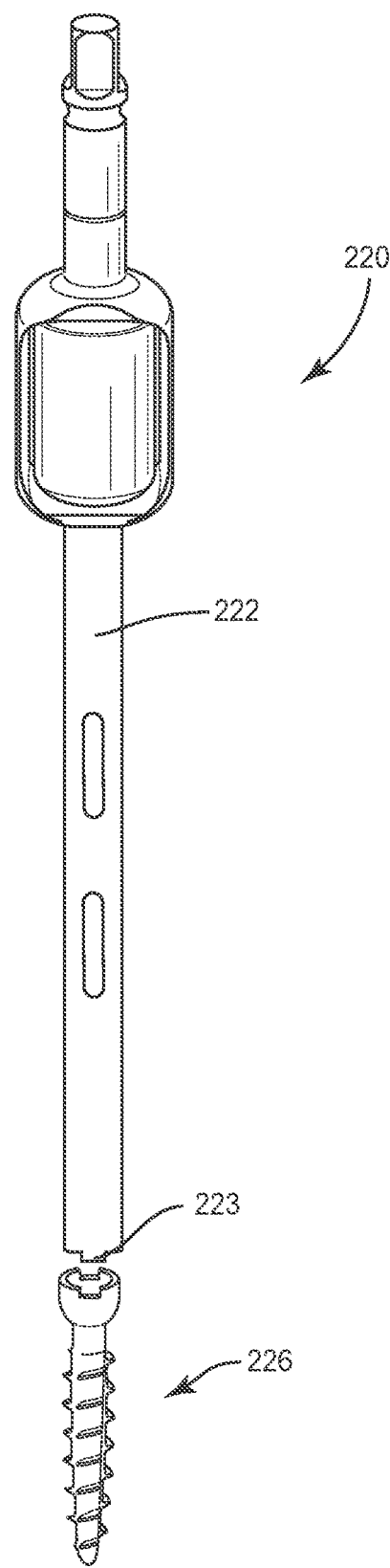
FIG. 15 is a perspective view of components of one embodiment of a surgical system in accordance with the principles of the present disclosure.

In some embodiments, in a step 750, alignment of channel 84 with screw trajectory T1 is maintained and the surgeon positions a tap instrument 200 within the surgical pathway of channel 84. Tap instrument 200, as shown in FIG. 14, forms threads in vertebral tissue about the pilot hole to facilitate fixation and positioning of screw shaft 22 with vertebra V1 along screw trajectory T1 and according to implant strategy 420. Tap instrument 200 includes a shaft 202 and a handle 204. In some embodiments, tap 200 is configured for connection with an actuator, such as, for example, a motorized actuator, such as, for example, a powered drill (not shown). Tap instrument 200 includes a cavity configured for insertion and internal connection of a threaded tap 206 configured to form an internal or female thread in tissue such that screw shaft 22 can be threaded into the internal thread formed by tap instrument 200. Tap instrument 200 is actuated to create threads in vertebral tissue about the pilot hole and removed from the surgical pathway of channel 84. In some embodiments, a tap instrument 220, as shown in FIG. 15, is employed with robot 86, similar to tap instrument 200. Tap instrument 220 forms threads in vertebral tissue about the pilot hole to facilitate fixation and positioning of screw shaft 22 with vertebra V1 along screw trajectory T1 and according to implant strategy 420. Tap instrument 220 includes a shaft 222 and a handle 224. Tap 220 includes tabs 223 configured for engagement with recesses of a threaded tap 226 in an external connection with threaded tap 226 to form an internal or female thread in tissue such that screw shaft 222 can be threaded by tap instrument 220.

In a surgical step 760, alignment of channel 84 with screw trajectory T1 is maintained and prior to manipulation of vertebrae V, for example, decompression, disc preparation and/or interbody insertion, screw shafts 22 are engaged with vertebrae V. For example, screw shaft 22 is connected with driver 18, as described herein. The surgeon positions driver 18 with screw shaft 22 extending therefrom within the surgical pathway of channel 84. Driver 18 is translated by the surgeon through the surgical pathway of channel 84 in alignment with screw trajectory T1. Screw shaft 22 engages vertebra V1 and driver 18 is manipulated to drive, torque, insert or otherwise connect screw shaft 22 with the pilot hole of vertebra V1 along screw trajectory T1 and according to implant strategy 420, as shown in FIG. 16. Driver 18 is disengaged from screw shaft 22, as described herein and shown in FIG. 17. Driver 18 is removed from the surgical pathway of channel 84.

In some embodiments, implant strategy 420 includes a screw trajectory T2 of an insertion path and positioning of a screw shaft 22 with a contra-lateral side of vertebra V1, as shown in FIG. 13, similar to screw trajectory T1 described herein. Arm 14 is moved to align channel 84 with screw trajectory T2 and define a surgical pathway along screw trajectory T2 to vertebra V1, similar to that described with regard to step 730. An incision and pilot hole are created in vertebra V1 along screw trajectory T2, similar to that described with regard to step 740. In some embodiments, a tap instrument may be used to form threads in vertebral tissue about the pilot hole of vertebra V1 along screw trajectory T2, similar to that described with regard to step 750. Driver 18 is connected with screw shaft 22, which engages vertebra V1 along screw trajectory T2 and according to implant strategy 420, similar to that described with regard to step 760.

In some embodiments, implant strategy 420 includes screw trajectories T3, T4 of insertion paths and positioning of screw shafts 22 with a lateral and contra-lateral side, respectively, of vertebra V2, as shown in FIG. 13, similar to screw trajectories T1, T2 described herein. Arm 14 is moved to align channel 84 and define respective surgical pathways along screw trajectories T3, T4 to vertebra V2, similar to that described with regard to step 730. Incisions and pilot holes are created in vertebra V2 along screw trajectories T3, T4, similar to that described with regard to step 740. In some embodiments, a tap instrument may be used to form threads in vertebral tissue about the pilot holes of vertebra V2 along screw trajectories T3, T4, similar to that described with regard to step 750. Driver 18 is connected with screw shafts 22, which engage vertebra V2 along screw trajectories T3, T4, respectively, and according to implant strategy 420, similar to that described with regard to step 760. In some embodiments, implant strategy 420 may include one or a plurality of screw insertion paths and/or trajectories.

With one or more screw shafts 22 engaged with vertebrae V, as described during surgery 700, vertebrae V is subsequently manipulated in a step 770 for selected treatment in connection with a surgical procedure, as described herein. In some embodiments, robot 86 and/or arm 14 can be moved out alignment with the screw trajectories, or withdrawn from the surgical site. For example, in a step 800, a decompression instrument, such as, for example, a distractor (not shown) is attached with heads 26 of screw shafts 22. The distractor manipulates vertebrae V to rotate, for example, vertebra V2 relative to vertebra V1 to decompress intervertebral space S between vertebrae V, relieve disc pressure, realign one or more vertebra and/or reduce compression on the spinal cord and adjacent nerves.

In some embodiments, manipulation step 770 can include a step 810, which includes discectomy performed, for example, between vertebra V1 and vertebra V2 for selected treatment in connection with a surgical procedure, as described herein. A discectomy instrument, such as, for example, a cutter (not shown) is employed to engage tissue between vertebra V1 and vertebra V2 at the surgical site. The cutter is manipulated to disrupt and/or remove tissue to form a cavity in vertebral space S, as shown in FIG. 13. In some embodiments, implant strategy 420 may include surgical parameters for creating a surgical pathway for discectomy and channel 84 can be employed to facilitate delivery of the cutter to vertebral space S and discectomy, similar to that described with regard to surgery 700.

In some embodiments, manipulation step 770 can include a step 820, which includes interbody devices (not shown) being implanted with vertebral space S for selected treatment in connection with a surgical procedure, as described herein. An inserter (not shown) is connected with an interbody cage for disposal with vertebral space S. In some embodiments, implant strategy 420 may include surgical parameters for creating a surgical pathway for implant of an interbody device and channel 84 can be employed to facilitate delivery of the interbody device to vertebral space S for implant, similar to that described with regard to surgery 700.

Figure 5:
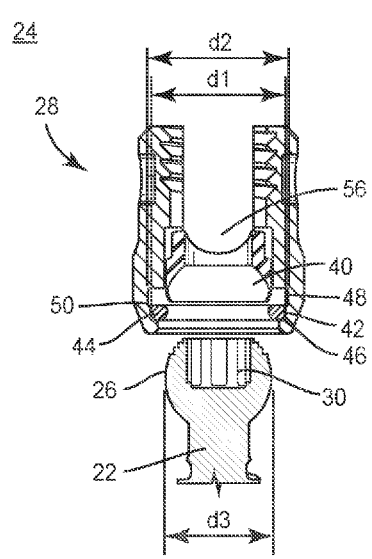
FIG. 5 is a side, cross section view of components of one embodiment of a surgical system in accordance with the principles of the present disclosure.
Figure 6:
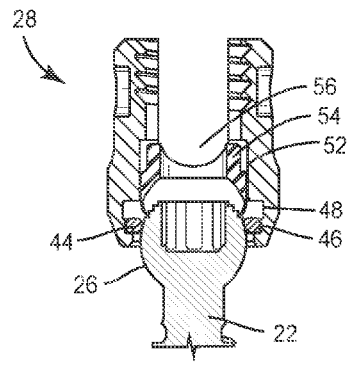
FIG. 6 is a side view of the components shown in FIG. 5.
Figure 7:
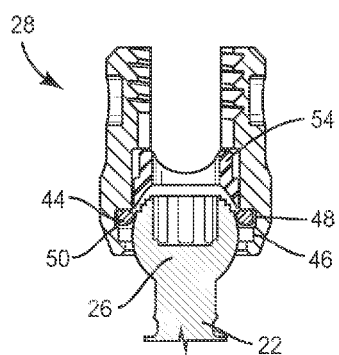
FIG. 7 is a side view of the components shown in FIG. 5.
Figure 8:
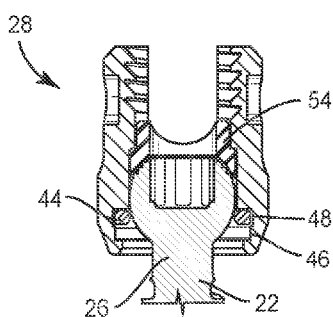
FIG. 8 is a side view of the components shown in FIG. 5.

In some embodiments, during surgery 700, in a step 780, a receiver 28 is selected and manipulated for attachment with each screw shaft 22 to form bone fastener 24 having a selected movement, as described herein. Receiver 28 includes ring 44 disposed in channel 46 in a contracted and/or capture orientation having a diameter d1, as shown in FIG. 5. In some embodiments, receiver 28 is manually engaged with head 26, as shown in FIG. 6, such that ring 44 translates from channel 46 into channel 48 over lip 50, as shown in FIG. 7. As head 26 engages ring 44, ring 44 expands to an expanded orientation, as shown in FIG. 7, and head 26 passes through ring 44. In the expanded orientation, ring 44 expands to diameter d2 (FIG. 5) in channel 48. Diameter d3 of head 26 passes through ring 44, as shown in FIG. 8, and the resiliency of ring 44 causes ring 44 to contract and translate along the surface of head 26. As ring 44 contracts back to the capture orientation, ring 44 translates over lip 50 into channel 46, as shown in FIG. 9. Diameter d3 of head 26 prevents head 26 from moving through ring 44 when ring 44 returns to channel 46. In some embodiments, implant strategy 420 may include surgical parameters for delivery and attachment of receiver 28 employing surgical robotic guidance system 12 and/surgical navigation system 16.

In some embodiments, during surgery 700, a step 790 includes attaching spinal rods (not shown) with vertebrae V. A rod inserter (not shown) is connected with a spinal rod. The spinal rod is positioned along vertebrae V and disposed with cavities 56 of receivers 28 attached with screw shafts 22 fastened with a lateral side of vertebra V1 and vertebra V2. A second spinal rod is similarly disposed with cavities 56 of receivers 28 attached with screw shafts 22 fastened with a contra-lateral side of vertebra V1 and vertebra V2. A rod reducer (not shown) is translated into alignment with the surgical site. The spinal rods are reduced into cavities 56. Set screws (not shown) are delivered into engagement with receivers 28. A driver (not shown) is actuated to engage the set screws with receivers 28 to fix the spinal rods with vertebrae V.

Upon completion of a procedure, the surgical instruments and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical method comprising:
providing a first image comprising a representation of anatomy of a patient;
pre-operatively generating a second image comprising a representation of at least a portion of a robot;
registering the first image with the second image to generate a third image; and
engaging an implant with the anatomy via robotic guidance based on the third image.

2. The method recited in claim 1, wherein the implant is a screw and engaging the implant with the anatomy comprises threading the screw into tissue.

3. The method recited in claim 1, wherein the implant is a screw and the method further comprises manually engaging an implant receiver with the screw to connect the implant receiver to the screw.

4. The method recited in claim 3, wherein manually engaging the implant receiver with the screw includes snap fitting the screw with the implant receiver in a non-instrumented assembly.

5. The method recited in claim 1, further comprising manipulating the anatomy after engaging the implant with the anatomy.

6. The method recited in claim 5, manipulating the anatomy includes decompressing vertebrae.

7. The method recited in claim 5, manipulating the anatomy includes discectomy.

8. The method recited in claim 1, further comprising inserting an interbody implant between first and second vertebrae of the anatomy.

9. The method recited in claim 1, further comprising drilling a pilot hole in tissue of the anatomy via robotic guidance prior to engaging the implant with the anatomy.

10. The method recited in claim 1, further comprising tapping tissue of the anatomy via robotic guidance prior to engaging the implant with the anatomy.

11. The method recited in claim 1, further comprising pre-operatively generating three dimensional images of the anatomy to produce the first image.

12. The method recited in claim 1, further comprising pre-operatively generating a CT scan of the anatomy to produce the first image.

13. The method recited in claim 1, further comprising generating a scan with an O-Arm imaging device intra-operatively to produce the first image.

14. The method recited in claim 1, wherein:
the implant includes a plurality of pedicle screws;
the method further comprises selecting an implant strategy for the implant;
the screws are engaged with the anatomy according to the implant strategy; and
the implant strategy includes a plurality of screw trajectories for positioning the screws with a first vertebra and a second vertebra of the anatomy.

15. A method as recited in claim 1, further comprising:
connecting the implant with an instrument; and
inserting the instrument through an incision to engage the implant with the anatomy,
wherein the second image is generated before the instrument is inserted through the incision.

16. A surgical method:
pre-operatively generating a CT scan of patient anatomy including a spine;
pre-operatively generating fluoroscopic images of at least a portion of a robot;
registering the CT scan with the fluoroscopic images to generate a registered image; and
engaging a shaft with the spine via robotic guidance based on the registered image.

17. The method recited in claim 16, further comprising decompressing the spine after engaging the shaft with the spine.

18. The method recited in claim 16, further comprising manually engaging an implant receiver with the shaft to comprise a spinal construct.

19. A surgical method:
imaging vertebral tissue;
pre-operatively generating an image of a robot connected with the vertebral tissue;
registering the imaging of the vertebral tissue with the image of the robot to generate a registered image;
connecting a surgical driver with a bone screw shaft, the surgical driver including an image guide oriented relative to a sensor to communicate a signal representative of a position of the bone screw shaft;
engaging the bone screw shaft with the vertebral tissue via robotic guidance based on the registered image;
subsequently, manipulating the vertebral tissue; and
manually engaging an implant receiver with the bone screw shaft to comprise a bone screw.

20. The method recited in claim 19, wherein the step of manually engaging includes snap fitting the implant receiver with the bone screw shaft in a non-instrumented assembly.

* * * * *